US012765762B2

(12) United States Patent
Jeon et al.

(10) Patent No.: US 12,765,762 B2
(45) Date of Patent: Oct. 20, 2026

(54) INTRAORAL SCANNER

(71) Applicant: ARCREAL INC., Seoul (KR)

(72) Inventors: Seung Hyun Jeon, Seoul (KR); Kyong Kook Kim, Seoul (KR)

(73) Assignee: ARCREAL INC., Seoul (KR)

( * ) Notice: Subject to any disclaimer, the term of this patent is extended or adjusted under 35 U.S.C. 154(b) by 64 days.

(21) Appl. No.: 18/704,545

(22) PCT Filed: Oct. 31, 2022

(86) PCT No.: PCT/KR2022/016818
§ 371 (c)(1),
(2) Date: Apr. 25, 2024

(87) PCT Pub. No.: WO2023/075545
PCT Pub. Date: May 4, 2023

(65) Prior Publication Data

US 2025/0009219 A1 Jan. 9, 2025

(30) Foreign Application Priority Data

Oct. 29, 2021 (KR) ........................ 10-2021-0146626
Oct. 28, 2022 (KR) ........................ 10-2022-0141640

(51) Int. Cl.
*A61B 1/24* (2006.01)
*A61B 1/00* (2006.01)

(52) U.S. Cl.
CPC ............ *A61B 1/24* (2013.01); *A61B 1/00172* (2013.01); *A61B 1/00177* (2013.01)

(58) Field of Classification Search
CPC ............ A61B 1/00172; A61B 1/00177; A61B 1/00194; A61B 1/0605; A61B 1/24; A61B 1/00; A61B 1/247; A61C 9/006
See application file for complete search history.

(56) References Cited

U.S. PATENT DOCUMENTS 4,174,884 A * 11/1979 Weissler ................ G03B 35/18
359/471
4,575,805 A * 3/1986 Moermann ........ G05B 19/4207
433/55

(Continued)

FOREIGN PATENT DOCUMENTS

CN 108478177 B * 11/2020 ........... A61B 5/0088
EP 2950745 B1 * 11/2018 ............. A61C 9/006

(Continued)

OTHER PUBLICATIONS

Riehemann [Micro-Display-Based Intraoral 3D Scanner for Dentistry, Journal Of Display Technology, vol. 7, No. 3, Mar. 2011]. (Year: 2011).*

(Continued)

*Primary Examiner* — Oommen Jacob
(74) *Attorney, Agent, or Firm* — The PL Law Group, PLLC

(57) ABSTRACT

An intraoral scanner according to an embodiment includes a case having an opening part formed at one end thereof, a light source part disposed inside the case and configured to emit light, a first optical system including a first reflector configured to reflect the light emitted from the light source part and a second reflector configured to reflect the light reflected by the first reflector toward the opening part, a second optical system disposed in the opening part and configured to reflect the light reflected from the first optical system toward a subject located outside the case and reflect light reflected from the subject toward the inside of the case, a third optical system including reflectors and a prism configured to refract the light reflected from the second optical system, and an image sensor part configured to detect the light refracted by the third optical system.

11 Claims, 4 Drawing Sheets

(56) References Cited

U.S. PATENT DOCUMENTS 4,669,837 A * 6/1987 Schirmer ............. B23K 26/032 351/205
4,836,188 A * 6/1989 Berry ................. A61B 1/00193 600/102
5,385,138 A * 1/1995 Berry ................. A61B 1/00193 359/368
5,633,853 A * 5/1997 Kim ....................... G11B 17/22 369/197
5,715,489 A * 2/1998 Inaba ..................... G03B 35/10 396/386
5,835,133 A * 11/1998 Moreton ................ G02B 30/24 348/54
6,081,371 A * 6/2000 Shioda ............... G02B 21/0012 359/372
6,154,315 A * 11/2000 Street ................. A61B 1/00188 348/45
6,325,794 B1 * 12/2001 Yoon ...................... A61B 18/22 606/17
6,810,140 B2 * 10/2004 Yang ...................... A61B 3/102 382/128
7,217,241 B2 * 5/2007 Guenier ............. A61B 1/00149 600/172
7,405,877 B1 * 7/2008 Schechterman ... A61B 1/00096 359/464
7,986,415 B2 * 7/2011 Thiel .................... A61C 9/0053 356/608
8,149,270 B1 * 4/2012 Yaron .................. H04N 13/229 348/45
8,228,591 B1 * 7/2012 Towers ................... G01S 17/04 359/275
8,784,301 B2 * 7/2014 McDowall ......... G02B 23/2415 600/129
9,039,418 B1 * 5/2015 Rubbert ............. H04N 1/00026 433/215
9,860,520 B2 * 1/2018 Michaeli ................ A61B 1/247
10,456,043 B2 * 10/2019 Atiya ..................... A61B 1/247
2001/0055150 A1 * 12/2001 Ito .......................... G02B 21/22 359/368
2003/0072570 A1 * 4/2003 Seo ...................... H04N 13/218 348/E13.02
2003/0107652 A1 * 6/2003 Williams ............... A61B 1/042 348/E5.025
2003/0174237 A1 * 9/2003 Lee ...................... H04N 13/211 348/E13.009
2004/0117052 A1 * 6/2004 Geng ................. A61B 1/00142 700/117
2004/0220464 A1 * 11/2004 Benninger ........... A61B 5/0059 600/407
2005/0245917 A1 * 11/2005 Strassl ................. A61C 1/0046 606/17
2007/0232860 A1 * 10/2007 Kubo ................. A61B 1/00096 600/160
2010/0253773 A1 * 10/2010 Oota ...................... G01B 11/25 356/445
2012/0040305 A1 * 2/2012 Karazivan .......... A61B 1/00087 433/29
2013/0038689 A1 * 2/2013 McDowall ............. H04N 23/10 348/45
2013/0093858 A1 * 4/2013 Lee ........................ G02B 30/24 348/49
2013/0250061 A1 * 9/2013 Hofer ................. A61B 1/00193 348/45
2014/0248576 A1 * 9/2014 Tchouprakov ....... A61C 9/0073 433/29
2016/0045291 A1 * 2/2016 Verker ................. A61C 9/0066 356/364
2017/0026570 A1 * 1/2017 Shepard ..................... G01J 3/12
2017/0299553 A1 * 10/2017 Fukushima ............ G01N 29/06
2019/0029784 A1 * 1/2019 Moalem .................. G06T 17/00
2019/0247163 A1 8/2019 Wu et al.
2020/0205942 A1 * 7/2020 Pesach ................. G06V 20/653
2020/0345471 A1 * 11/2020 Schmid ................ A61C 19/004
2024/0090984 A1 * 3/2024 Jeon ........................ G02B 17/04
2025/0009219 A1 * 1/2025 Jeon ................... A61B 1/00172
2025/0049312 A1 * 2/2025 Jeon ........................ A61C 9/006

FOREIGN PATENT DOCUMENTS

EP 3616598 A1 * 3/2020 ............. H04N 7/183
KR 10-1371211 B1 3/2014
KR 10-1533341 B1 7/2015
KR 10-1611415 B1 4/2016
KR 10-1662566 B1 10/2016
KR 10-2018-0024477 A 3/2018
KR 20180024477 A * 3/2018 ........... A61B 5/0088
KR 10-2341890 B1 12/2021
KR 102458838 B1 * 10/2022 ........... A61C 9/0053
WO WO 2014/144434 A1 9/2014
WO WO 2015/133824 A1 9/2015

OTHER PUBLICATIONS

Silvia [Recentadvancesindentaloptics—PartI:3Dintraoralscanners for restorativedentistry, Optics andLasersinEngineering54(2014) 203-221] (Year: 2014).*

Chintal [Development of 3-Dimensional Miniaturized Scanning System for Dentistry, University of Ulsan School of Mechanical & Automotive Engineering] (Year: 2016).*

International Search Report for PCT/KR2022/016818 mailed on Feb. 10, 2023.

Office action issued on Jul. 11, 2024 from Korean Patent Office in a counterpart Korean Patent Application No. 10-2022-0141640 (all the cited references are listed in this IDS.) (English translation is also submitted herewith.).

Office action issued on Mar. 12, 2025 from Korean Patent Office in a counterpart Korean Patent Application No. 10-2022-0141640 (all the cited references are listed in this IDS.) (English translation is also submitted herewith.).

Notice of Allowance issued on Nov. 10, 2025 from Korean Patent Office in a counterpart Korean Patent Application No. 10-2022-0141640 (all the cited references are listed in this IDS.) (English translation is also submitted herewith.).

European Search Report For EP 22887739.5ssued on Jan. 9, 2025 from European patent office in a counterpart European patent application.

* cited by examiner

INTRAORAL SCANNER

CROSS REFERENCE TO RELATED APPLICATIONS AND CLAIM OF PRIORITY

This application claims benefit under 35 U.S.C. 119, 120, 121, or 365 (c), and is a National Stage entry from International Application No. PCT/KR2022/016818 filed on Oct. 31, 2022, which claims priority to the benefit of Korean Patent Application Nos. 10-2021-0146626 filed on Oct. 29, 2021 and 10-2022-0141640 filed on Oct. 28, 2022 in the Korean Intellectual Property Office, the entire contents of which are incorporated herein by reference.

BACKGROUND

1. Technical Field

The present disclosure relates to an intraoral scanner, and more particularly, to an intraoral scanner configured to obtain a 3D image of an oral cavity.

2. Background Art

Generally, an impression-taking procedure is performed in a process of diagnosis or treatment of a dental patient. Impression taking is a necessary clinical procedure in establishing a diagnosis and treatment plan for a patient by reflecting conditions of teeth and tissue in an oral cavity in an impression material. In recent years, with application of digital technology to dental clinic and lab processes, the number of cases of using a digital impression in which an oral cavity or an impression body is scanned and converted into digital data without using an impression material in impression taking has increased. In this way, with an increase in the importance of a digital impression in dental diagnosis and treatment, development of technology related to intraoral scanners has been actively carried out.

An intraoral scanner is a device or system inserted into an oral cavity of a dental patient to scan a 3D structure of teeth in a non-contact manner. Generally, recently developed intraoral scanners capture 2D image data of an oral cavity and perform 3D modeling of an oral cavity structure based on the 2D image data. The range of application of intraoral scanners having such functions has expanded among clinical applications, and the intraoral scanners may also be used in fabricating an implant, an orthodontic appliance, and the like in addition to being used in treatment for tooth restoration.

Meanwhile, impression accuracy is important for successful dental treatment. A digital impression using an intraoral scanner does not have a problem of deformation due to contraction, expansion, or the like of an impression material and thus has higher impression accuracy compared to a traditional impression-taking method. However, for an intraoral scanner to be continuously used as a tool for sophisticated dental treatment, there is a need to enhance scanning accuracy. Also, since an intraoral scanner is used by being inserted into an oral cavity of a dental patient in a non-contact manner, it is preferable for the intraoral scanner to have a structure that makes a patient feel comfortable during use of the intraoral scanner.

SUMMARY

Embodiments disclosed in the present specification provide an intraoral scanner having a plurality of optical systems disposed therein to have a structure suitable to be used by being inserted into an oral cavity of a dental patient in a non-contact manner.

One embodiment of the present disclosure provides an intraoral scanner including: a case having an opening part formed at one end thereof: a light source part disposed inside the case and configured to emit light: a first optical system including a first reflector configured to reflect the light emitted from the light source part and a second reflector configured to reflect the light reflected by the first reflector toward the opening part: a second optical system disposed in the opening part and configured to reflect the light reflected from the first optical system toward a subject located outside the case and reflect light reflected from the subject toward the inside of the case; a third optical system including reflectors and a prism configured to refract the light reflected from the second optical system; and an image sensor part configured to detect the light refracted by the third optical system.

According to one embodiment, the third optical system may include a first reflector and a second reflector configured to reflect the light reflected from the second optical system and a prism configured to refract the light reflected by the first reflector and the second reflector toward the image sensor part, and the first reflector and the second reflector may be disposed to be symmetrical to each other about the prism.

According to one embodiment, a dihedral angle between the first reflector and the second reflector may be configured to form a minor angle.

According to one embodiment, positions and directions of the first reflector, the second reflector, and the prism may be set so that a plurality of images of the subject each refracted by the prism and detected by the image sensor part do not overlap with each other, and each of the images is entirely visible.

According to one embodiment, the first optical system may be configured as a rhomboid prism including the first reflector and the second reflector.

According to one embodiment, the light source part may include a first light source part disposed at an upper portion from the image sensor part and a second light source part disposed at a lower portion from the image sensor part.

According to one embodiment, in the first optical system, the first reflector may be configured to reflect light emitted from the first light source part, a third reflector disposed at a position symmetrical to the first reflector about the second reflector and configured to reflect light emitted from the second light source part may be further included, the second reflector may include two reflective surfaces each configured to reflect one of the light reflected by the first reflector and the light reflected by the third reflector toward the opening part, and a dihedral angle between the reflective surfaces of the second reflector may be configured to form a major angle.

According to one embodiment, the light source part may be configured to emit patterned light or structured light.

According to one embodiment, the image sensor part may be configured to obtain a plurality of stereo images from an image of light reflected from the third optical system.

According to one embodiment, virtual central lines of the light source part, the first optical system, the second optical system, the third optical system, and the image sensor part that are projected on a plane of the case may be arranged to be aligned on a virtual central line projected on the plane of the case.

According to various embodiments of the present disclosure, since a driving part for angle adjustment of each of a plurality of optical systems disposed inside a case of an intraoral scanner is unnecessary, the optical systems can be densely arranged at optimal positions inside the case.

Also, according to various embodiments of the present disclosure, since it is possible to implement an intraoral scanner having a small volume by arranging a plurality of optical systems in a dense structure inside a case, during use of the intraoral scanner, it is not only easy to insert the intraoral scanner into an oral cavity of a dental patient but also easy to move or change a direction of the intraoral scanner in the oral cavity, and thus dental scanning can be precisely performed.

In addition, according to various embodiments of the present disclosure, since two or more stereo images can be obtained from images of light reflected from a plurality of optical systems with only a single image sensor part, manufacturing costs of an intraoral scanner can be reduced, and an internal configuration thereof can be further optimized.

Advantageous effects of the present disclosure are not limited to those mentioned above, and other unmentioned advantageous effects should be clearly understood by those of ordinary skill in the art from the claims below.

DETAILED DESCRIPTION

Figure 1:
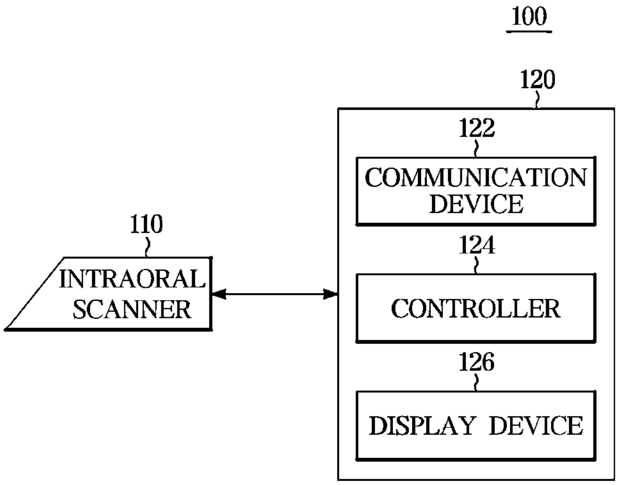
FIG. 1 is a block diagram illustrating a configuration in which an intraoral scanner according to one embodiment of the present disclosure is connected to an intraoral 3D modeling and visualization system.

Hereinafter, details for carrying out the present disclosure will be described in detail with reference to the accompanying drawings. However, in the description below, when there is concern about unnecessarily obscuring the gist of the present disclosure, detailed description of a widely known function or configuration will be omitted.

In the accompanying drawings, the same or corresponding components are denoted by the same reference numerals. Also, in the following description of embodiments, repeated description of the same or corresponding components may be omitted. However, omission of description of a certain component may not mean that the component is not included in a certain embodiment.

Terms used in the present disclosure will be briefly described, and embodiments disclosed herein will be described in detail. General terms that are currently widely used have been selected as terms used herein in consideration of functions in the present disclosure, but the terms may be changed according to an intention or practice of those of ordinary skill in the art, the advent of new technology, and the like. Also, in some cases, some terms may have been arbitrarily selected by the applicant, and in such cases, the meanings of the terms will be described in detail in the corresponding part of the description of the invention. Therefore, the terms used in the present disclosure should be defined based on the meanings of the terms and the content throughout the present disclosure, instead of being simply defined based on the names of the terms.

In the present disclosure, a singular expression includes a plural expression unless the context clearly indicates singularity. Also, a plural expression includes a singular expression unless the context clearly indicates plurality.

In the present disclosure, when a certain part is described as including a certain component, this indicates that the certain part may further include other components instead of excluding other components unless the context clearly indicates otherwise.

In the present disclosure, the upper part of a drawing may be referred to as “upper portion” or “upper side” of a configuration illustrated in the drawing, and the lower part of the drawing may be referred to as “lower portion” or “lower side” of the configuration Also, a portion between the upper portion and the lower portion of the configuration illustrated in the drawing or a remaining portion excluding the upper portion and the lower portion may be referred to as “side portion” or “side surface” of the configuration. The relative terms such as “upper portion” and “upper side” may be used to describe the relationship between configurations illustrated in the drawings, and the present disclosure is not limited by the terms.

In the present disclosure, a direction toward an inner space of one structure may be referred to as “inner side,” and a direction protruding to an open outer space may be referred to as “outer side.” The relative terms such as “inner side” and “outer side” may be used to describe the relationship between configurations illustrated in the drawings, and the present disclosure is not limited by the terms.

In the present disclosure, the term “A and/or B” refers to A, B, or A and B.

In the present specification, when a certain part is described as being connected to another part, this not only includes a case in which the two parts are directly connected but also includes a case in which the two parts are connected with another configuration disposed therebetween.

Also, terms such as “module” or “part” used in the present disclosure refer to software or hardware components, and a “module” or “part” performs a certain role. However, the meaning of “module” or “part” is not limited to software or hardware. A “module” or “part” may be configured to be present in addressable storage media or configured to replay one or more processors. Therefore, as one example, a “module” or “part” may include at least one of components such as software components, object-oriented software components, class components, and task components, processes, functions, attributes, procedures, subroutines, program code segments, drivers, firmware, micro codes, circuits, data, databases, data structures, tables, arrays, or variables. The components and the “modules” or “parts” and functions provided therein may be combined into a smaller number of components and “modules” or “parts” or may be further separated into a larger number of components and “modules” or “parts.”

Advantages and features of the embodiments disclosed herein and methods of achieving the same should become clear from embodiments described in detail below with reference to the accompanying drawings. However, the present disclosure is not limited to the embodiments disclosed below and may be implemented in various different forms. The present embodiments are only provided to make the present disclosure complete and completely inform those of ordinary skill in the art to which the present disclosure pertains of the scope of the invention.

FIG. 1 is a block diagram illustrating a configuration of an intraoral scanning system 100 in which an intraoral scanner 110 according to one embodiment of the present disclosure is connected to an intraoral 3D modeling and visualization server 120. As illustrated, the intraoral scanning system 100 may include the intraoral scanner 110 that can scan a 3D structure of an oral cavity of a dental patient and the intraoral 3D modeling and visualization server 120 connected to the intraoral scanner 110.

For example, the intraoral scanner 110 may be inserted into an oral cavity of a dental patient by a medical worker in a dental clinic to scan teeth in a non-contact manner and capture a plurality of pieces of 2D image data. Also, the intraoral scanner 110 may send the plurality of pieces of captured 2D image data to the 3D modeling and visualization server 120 or may perform 3D oral cavity structure modeling based on the 2D image data by itself.

The intraoral scanner 110 may be connected to the 3D modeling and visualization server 120 through a network configured to be able to communicate via a wire or wirelessly. Here, for example, according to an installation environment, the network may be configured with a wired network such as an electric connection line such as a copper cable, Ethernet, a wired home network (power line communication), a phone line communication device, and RS-serial communication, a wireless network such as a mobile network, a wireless local area network (WLAN), Wi-Fi, Bluetooth, and ZigBee, or a combination thereof.

The intraoral scanner 110 may transmit and receive information and/or data such as 2D image data and 3D oral cavity structure model data to and from the 3D modeling and visualization server 120. The intraoral scanner 110 and the 3D modeling and visualization server 120 may be configured to be physically separated as illustrated, but the present disclosure is not limited thereto. For example, the intraoral scanner 110 and the 3D modeling and visualization server 120 may be integrally configured in a single computing device.

The 3D modeling and visualization server 120 may perform 3D oral cavity structure modeling based on at least two pieces of 2D image data or stereo images obtained from the intraoral scanner 110. In order to perform such functions, the 3D modeling and visualization server 120 may correspond to a computing device including a processor that can perform image processing and 3D modeling (for example, a central processing unit (CPU), a graphics processing unit (GPU), an application processor (AP), a neutral processing unit (NPU), etc.) and a memory that can store 2D image data and 3D oral cavity structure model data. In one embodiment, the 3D modeling and visualization server 120 may include a communication device 122, a controller 124, and a display device 126 as illustrated. The communication device 122 may be configured to transmit and receive information and/or data to and from the intraoral scanner 110. Specifically, the communication device 122 may transmit a command signal of the controller 124 to the intraoral scanner 110 and may receive image information of a target oral cavity structure from the intraoral scanner 110.

The controller 124 may control the intraoral scanner 110 to capture an image of the target oral cavity structure. Specifically, the controller 124 may control at least one or more light source parts (for example, 220 in FIG. 2) installed inside the intraoral scanner 110 to emit light toward at least one of a plurality of optical systems. Also, the controller 124 may control an image sensor part (for example, 260 in FIG. 2) installed inside the intraoral scanner 110 to detect light reflected by at least one of the plurality of optical systems. The controller 124 may control the image sensor part to obtain at least two or more stereo images from an image of the detected light. The controller 124 may control the display device 126 to display the two or more stereo images received from the intraoral scanner 110. Alternatively or additionally, the controller 124 may control 3D oral cavity structure model data calculated based on the two or more stereo images to be visualized and displayed on the display device 126.

The display device 126 may display information and/or data received from the intraoral scanner 110 or the controller 124. In this case, data displayed on the display device 126 may include two stereo images or 3D oral cavity structure model images. In one embodiment, the display device 126 may include a display panel device such as a light emitting diode (LED) display, an organic light emitting diode (OLED) display, a liquid crystal display (LCD), or a touch display.

Figure 2:
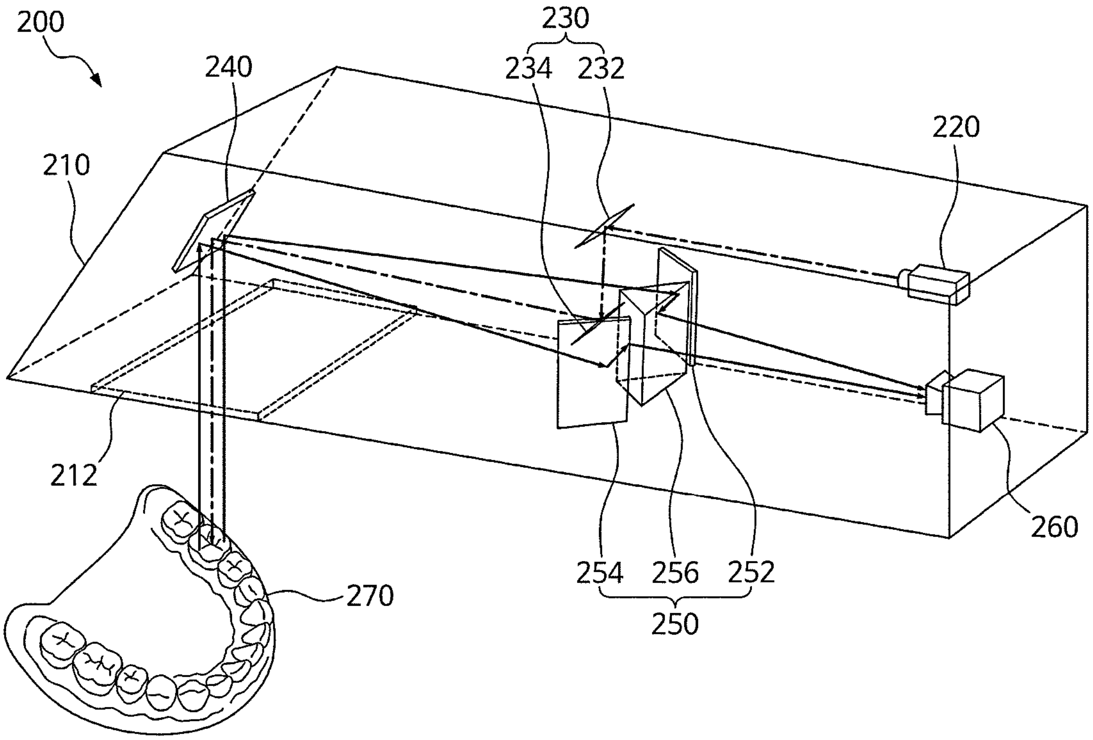
FIG. 2 is a see-through perspective view of an intraoral scanner according to one embodiment of the present disclosure.

FIG. 2 is a see-through perspective view of an intraoral scanner 200 according to one embodiment of the present disclosure. As illustrated in FIG. 2, the intraoral scanner 200 may include a case 210, a light source part 220, a first optical system 230, a second optical system 240, a third optical system 250, and an image sensor part 260.

The case 210 may be configured to form an exterior of the intraoral scanner 200 and accommodate the light source part 220, the first optical system 230, the second optical system 240, the third optical system 250, and the image sensor part 260 therein. As illustrated in FIG. 2, the case 210 may have the shape of a trapezoidal box that substantially extends in any one longitudinal direction, but the present disclosure is not limited thereto. For example, the case 210 may have a rectangular parallelepiped shape, a cylindrical shape, a streamlined shape, or any other shape suitable for insertion into an oral cavity.

An opening part 212 may be formed at one end of the case 210. Specifically, the opening part 212 may include an opening formed at one end of the case 210. In this case, the opening of the opening part 212 may be configured to allow light generated or reflected inside the case 210 to be emitted to the outside and external light to be introduced into the case 210. In one embodiment, the opening part 212 may be configured to be positioned at the innermost side of an oral cavity when the intraoral scanner 200 is inserted into the oral cavity.

The light source part 220 may be configured to emit light toward the opening part 212, the first optical system 230, or the second optical system 240. In this case, light emitted from the light source part 220 may correspond to patterned light or structured light. The light may have a linear pattern, a dot pattern, or any other pattern. When patterned light is emitted to a subject 270 such as teeth in an oral cavity located outside the case, deformation of the corresponding pattern may occur according to a 3D structure of a surface of the subject 270. Therefore, the 3D structure of the subject 270 may be identified and modeled based on the deformation of the pattern projected on the surface of the subject 270 or information on changes of positions of feature points.

The light source part 220 may be disposed inside the case 210. Specifically, the light source part 220 may be disposed to be accommodated at the other end inside the case 210 that faces one end of the case 210 at which the opening part 212 or the second optical system 240 is formed. For example, the light source part 220 may be disposed to be fixed to an upper portion of the other end inside the case 210. In one embodiment, the light source part 220 may include a first light source part (for example, 722 in FIG. 7) and a second light source part (for example, 724 in FIG. 7). In this case, the first light source part and the second light source part may be disposed at the other end of the case together with the image sensor part 260 and may be disposed to be respectively fixed to the upper portion and lower portion of the other end inside the case 210 around the image sensor part. The configuration of the intraoral scanner 200 including the two light source parts will be described in detail below with reference to FIG. 7.

In one embodiment, the light source part 220 may be disposed at one side end of the case 210, but the present disclosure is not limited thereto. For example, the light source part 220 may be disposed at any intermediate point between one end and the other end of the case 210. That is, the light source part 220 may be disposed at any position inside the case 210 where it is easy for the light source part 220 to emit light toward the opening part 212, the first optical system 230, or the second optical system 240.

The first optical system 230 may be configured to reflect light emitted from the light source part 220 toward the second optical system 240 or the opening part 212. As illustrated in FIG. 2, the first optical system 230 may include a first reflector 232 and a second reflector 234. The first reflector 232 may be configured to reflect light emitted from the light source part 220 toward the second reflector 234. The first reflector 232 may be disposed to be fixed to an upper portion inside the case. Also, the second reflector 234 may be configured to reflect the light reflected by the first reflector 232 toward the second optical system 240 or the opening part 212. The second reflector 234 may be disposed to be spaced apart from the first reflector 232 and fixed to a central portion inside the case 210. That is, the light emitted from the light source part 220 may be reflected toward the second optical system 240 or the opening part 212 via the first reflector 232 and the second reflector 234 of the first optical system 230.

The second optical system 240 may be configured to reflect light emitted from the second reflector 234 of the first optical system 230 toward the subject 270 and reflect light reflected from the subject 270 toward the second reflector 234 or the third optical system 250. The second optical system 240 may include at least one reflector. For example, the second optical system 240 may be at least one mirror. In one embodiment, the second optical system 240 may be disposed at the opening part 212 or around the opening part 212. For example, the second optical system 240 may be disposed to be fixed to an inner side surface of the opening part 212.

The third optical system 250 may be configured to refract light emitted from the second optical system 240. Specifically, the third optical system 250 may refract light emitted from the second optical system 240 toward the image sensor part 260. In this case, the third optical system 250 may include a plurality of reflectors and a prism configured to refract light.

The third optical system 250 may be disposed to be adjacent to a back surface in the opposite direction of a reflective surface of the second reflector 234 of the first optical system 230. Specifically, the light source part 220 and the second optical system 240 may be disposed to be fixed to both ends of the space inside the case 210, the first optical system 230 may be disposed at any position between the light source part 220 and the second optical system 240, and the third optical system 250 may be disposed to be fixed to a position adjacent to the first optical system 230 in a direction in which the light source part 220 or the image sensor part 260 is positioned.

In one embodiment, the third optical system 250 may include a first reflector 252, a second reflector 254, and a prism 256. The first reflector 252 and the second reflector 254 may be configured to refract light reflected from the second optical system 240. Also, the prism 256 may be configured to refract the light reflected by the first reflector 252 and the second reflector 254 toward the image sensor part 260. Here, the first reflector 252 and the second reflector 254 may be disposed to be symmetrical to each other about the prism 256. For example, the first reflector 252 and the second reflector 254 may be disposed to be symmetrical about virtual central lines of the light source part 220, the first optical system 230, the second optical system 240, the prism 256 of the third optical system 250, and the image sensor part 260 that are projected on a plane of the case 210. Also, a dihedral angle between the first reflector 252 and the second reflector 254 may be configured to form a minor angle, and positions and directions of the first reflector 252, the second reflector 254, and the prism 256 may be set so that a plurality of images of the subject each refracted by the prism 256 and detected by the image sensor part 260 do not overlap with each other, and each of the images is entirely visible.

In one embodiment, each of the first optical system 230, the second optical system 240, and the third optical system 250 may be disposed to be fixed to a predetermined position inside the case 210. In this case, a driving part for angle adjustment of the first optical system 230, the second optical system 240, and the third optical system 250 may not be installed inside the case 210. In this way, since there is no need to arrange another electronic or mechanical component in an area inside the case where the first optical system 230, the second optical system 240, and the third optical system 250 are disposed, the components inside the case may be densely arranged. Therefore, since it is possible to design an optimal structure of the case 210 from a dense structure of the first optical system 230, the second optical system 240, and the third optical system 250, it is possible to freely perform a scanning operation in an oral cavity and implement the intraoral scanner 200 with a small volume.

The image sensor part 260 may be configured to detect light refracted from the third optical system 250. In one embodiment, the image sensor part 260 may be configured to obtain at least two stereo images from light refracted from the third optical system 250. Specifically, the image sensor part 260 may simultaneously obtain at least two images of light refracted by the first reflector 252, the second reflector 254, and the prism 256 of the third optical system 250. In this way, since the intraoral scanner 200 includes the third optical system 250 including the two reflectors 252 and 254, at least two stereo images can be obtained with only the single image sensor part 260. The at least two stereo images obtained by the image sensor part 260 may be used in 3D oral cavity structure modeling performed by a processor afterwards.

In one embodiment, the image sensor part 260 may be disposed at the other end of the case 210. Specifically, the image sensor part 260 may be disposed to be accommodated at the other end inside the case 210 to face the one end of the case 210 where the opening part 212 or the second optical system 240 is formed. For example, the image sensor part 260 may be disposed to be fixed to the lower portion inside the case 210 that is adjacent to the light source part 220.

Figure 3:
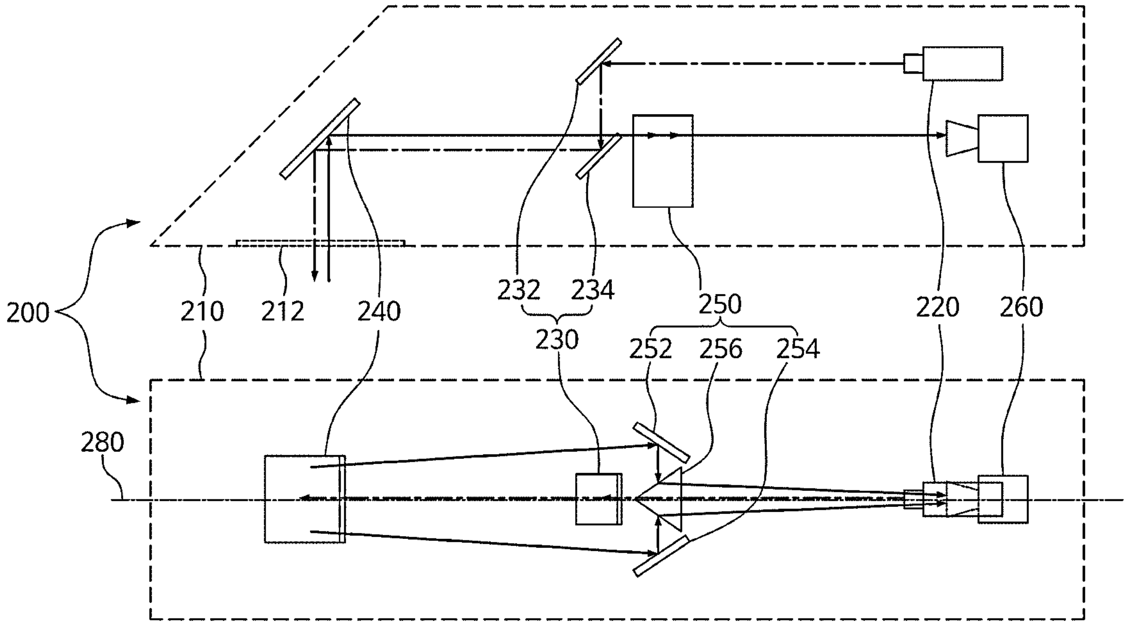
FIG. 3 shows a see-through lateral view and a see-through plan view of the intraoral scanner according to one embodiment of the present disclosure.

FIG. 3 shows a see-through lateral view and a see-through plan view of the intraoral scanner 200 according to one embodiment of the present disclosure. Configurations of FIG. 3 that overlap with FIG. 2 will be briefly described based on the embodiment illustrated in FIG. 3. In one embodiment, light may be emitted from the light source part 220 and may be reflected toward the second optical system 240 by the first reflector 232 and the second reflector 234 of the first optical system 230. Light reflected from the second reflector 234 may be reflected toward the subject positioned outside the case 210 by the second optical system 240. In this case, light may pass through an opening formed at one side of the opening part 212. Light reflected from the subject may be reflected toward the first reflector 252 and the second reflector 254 of the third optical system 250 by the second optical system 240. Light reflected by the first reflector 252 and the second reflector 254 may be refracted by the prism 256 and emitted toward the image sensor part 260.

In this case, the light source part 220 and the second optical system 240 may be disposed to be fixed to both ends of the space inside the case 210. Also, the first optical system 230 disposed at any position between the light source part 220 and the second optical system 240 may be disposed in an area that does not interfere with a path along which light that is reflected from the subject and reflected toward the third optical system 250 by the second optical system 240 passes, that is, a blind area. That is, the first optical system 230 may be disposed in an area that does not overlap with a portion of light reflected from the subject that is incident on the third optical system 250. For example, the first reflector 252 and the second reflector 254 of the third optical system 250 may be disposed to be spaced apart from each other on a rear surface of the second reflector 234, and a distance between the first reflector 252 and the second reflector 254 may correspond to a length of the width of the second reflector 234. In this way, by each of the first optical system 230 and the third optical system 250 being appropriately disposed in a blind area instead of a valid optical path while an optical path of the first optical system 230 and an optical path of the third optical system 250 do not interfere with each other, the components inside the case may be more densely arranged.

In one embodiment, the light source part 220, the first optical system 230, the second optical system 240, the third optical system 250, and the image sensor part 260 disposed inside the case 210 may be disposed to be axially aligned. For example, virtual central lines of the light source part 220, the first optical system 230, the second optical system 240, the third optical system 250, and the image sensor part 260 that are projected on a plane of the case may be arranged to be aligned on a virtual central line 280 projected on the plane of the case 210. With such a configuration, since it is possible to obtain two or more stereo images from images of light reflected from the plurality of optical systems with only the single image sensor part, manufacturing costs of the intraoral scanner can be reduced, and an internal configuration thereof can be further optimized.

Figure 4:
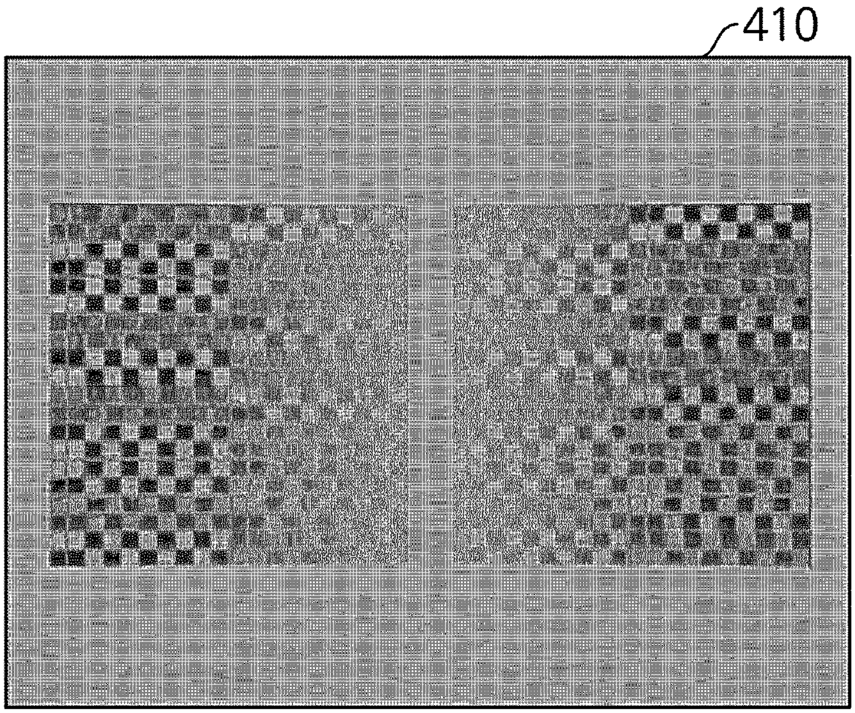
FIG. 4 is a view illustrating examples of stereo images obtained according to one embodiment of the present disclosure.

FIG. 4 is a view illustrating examples of stereo images 410 obtained according to one embodiment of the present disclosure. The image sensor part (for example, 260 in FIG. 2) may be configured to detect light refracted from the third optical system (for example, 250 in FIG. 2). In one embodiment, the image sensor part may be configured to obtain at least two stereo images 410 from light refracted from the third optical system. Specifically, the image sensor part may simultaneously obtain at least two stereo images which are obtained by light reflected by the first reflector and the second reflector of the third optical system being refracted by the prism. Based on the at least two stereo images obtained in this way, a processor may extract depth data and perform 3D modeling of an oral cavity structure, which is a subject, based on the depth data.

Although an example in which two stereo images are obtained is illustrated in FIG. 4, the present disclosure is not limited thereto, and the image sensor part may be configured to obtain more than two stereo images from light refracted from the third optical system.

Figure 5:
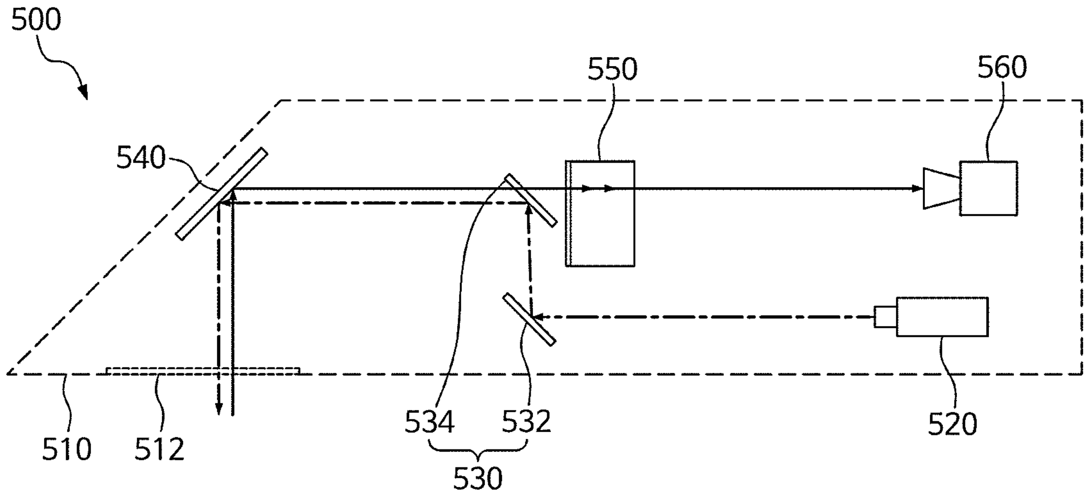
FIG. 5 is a see-through lateral view of an intraoral scanner according to another embodiment of the present disclosure.

FIG. 5 is a see-through lateral view of an intraoral scanner 500 according to another embodiment of the present disclosure. Configurations of FIG. 5 that overlap with FIG. 2 will be briefly described based on the embodiment illustrated in FIG. 5. As illustrated in FIG. 5, a light source part 520 may be configured to emit light toward an opening part 512 or a first optical system 530. The light source part 520 may be disposed to be accommodated at the other end inside a case 510 that faces one end of the case 510 at which the opening part 512 or a second optical system 540 is formed. For example, the light source part 520 may be disposed to be fixed to a lower portion of the other end inside the case 510.

In one embodiment, the first optical system 530 may be configured to, through a first reflector 532 and a second reflector 534, reflect light emitted from the light source part 520 toward the opening part 512 or the second optical system 540. Specifically, the first reflector 532 disposed to be fixed to a lower portion inside the case 510 may be configured to reflect light emitted from the light source part 520 toward the second reflector 534. Also, the second reflector 534 may be configured to reflect the light reflected by the first reflector 532 toward the opening part 512 or the second optical system 540. The second reflector 534 and the first reflector 532 may be disposed to be spaced apart from each other and fixed to a central portion inside the case 510.

Light reflected from the second reflector 534 may be reflected toward a subject outside the case by the second optical system 540. In this case, the light may pass through an opening formed at one side of the opening part 512. Light reflected from the subject may be reflected again toward a third optical system 550 by the second optical system 540. Light refracted by the third optical system 550 may be reflected toward an image sensor part 560. Here, the third optical system 550 may include the same configuration as the third optical system 250 illustrated in FIG. 2.

As illustrated, the light source part 520 and the second optical system 540 may be disposed to be fixed to both ends of the space inside the case 510. Also, the first optical system 530 disposed at any position between the light source part 520 and the second optical system 540 may be disposed in an area that does not interfere with a path along which light that is reflected from the subject and reflected toward the third optical system 550 by the second optical system 540 passes, that is, a blind area.

Figure 6:
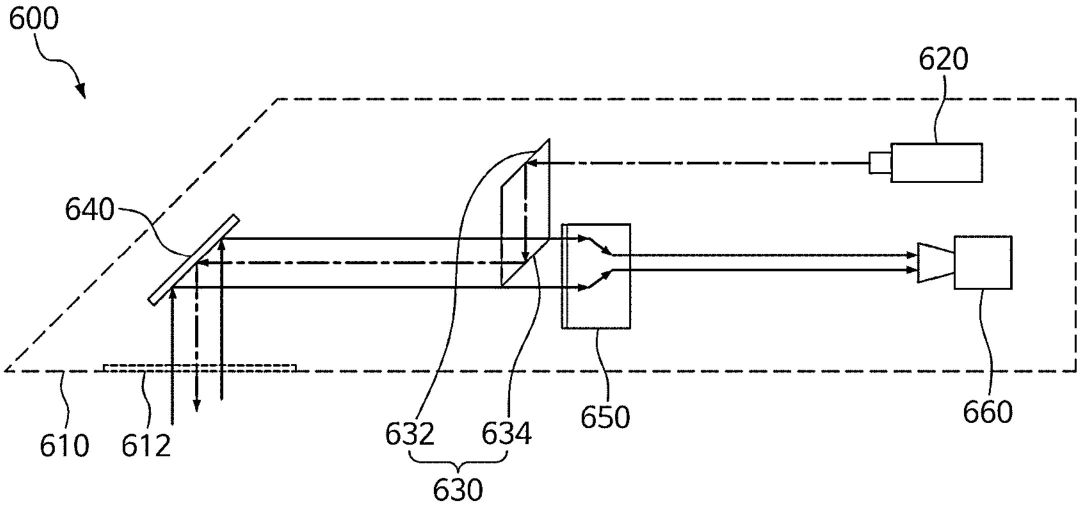
FIG. 6 is a see-through lateral view of an intraoral scanner according to still another embodiment of the present disclosure.

FIG. 6 is a see-through lateral view of an intraoral scanner 600 according to still another embodiment of the present disclosure. Configurations of FIG. 6 that overlap with FIG. 2 will be briefly described based on the embodiment illustrated in FIG. 6. As illustrated in FIG. 6, a light source part

620 may be configured to emit light toward an opening part 612 or a first optical system 630. The light source part 620 may be disposed to be accommodated at the other end inside a case 610 that faces one end of the case 610 at which the opening part 612 or a second optical system 640 is formed. For example, as illustrated, the light source part 620 may be disposed to be fixed to an upper portion of the other end inside the case 610. In another example, as illustrated in FIG. 5, the light source part 620 may be disposed to be fixed to a lower portion of the other end inside the case 610. In this case, a first reflector 632 and a second reflector 634 of the first optical system 630 may be disposed as illustrated in FIG. 5.

In one embodiment, the first optical system 630 may include a rhomboid prism including the first reflector 632 and the second reflector 634. In this case, light emitted from the light source part 620 may be reflected toward the opening part 612 through the first reflector 632 and the second reflector 634 of the prism. That is, the first reflector 632 of the prism may be configured to reflect the light emitted from the light source part 620 toward the second reflector 634. Also, the second reflector 634 may be configured to reflect the light reflected by the first reflector 632 toward the opening part 612 or the second optical system 640. That is, the light emitted from the light source part 620 may be reflected toward the second optical system 640 or the opening part 612 via the rhomboid prism of the first optical system 630.

Light reflected from the second reflector 634 of the rhomboid prism may be reflected toward a subject by the second optical system 640. In this case, light may pass through an opening formed at one side of the opening part 612. Light reflected from the subject may be reflected again toward a third optical system 650 by the second optical system 640. Light refracted by the third optical system 650 may be reflected toward an image sensor part 660. Here, the third optical system 650 may include the same configuration as the third optical system 250 illustrated in FIG. 2.

As illustrated, the light source part 620 and the second optical system 640 may be disposed to be fixed to both ends of the space inside the case 610. Also, the rhomboid prism, which is the first optical system 630 disposed at any position between the light source part 620 and the second optical system 640, may be disposed in an area that does not interfere with a path along which light that is reflected from the subject and reflected toward the third optical system 650 by the second optical system 640 passes, that is, a blind area.

Figure 7:
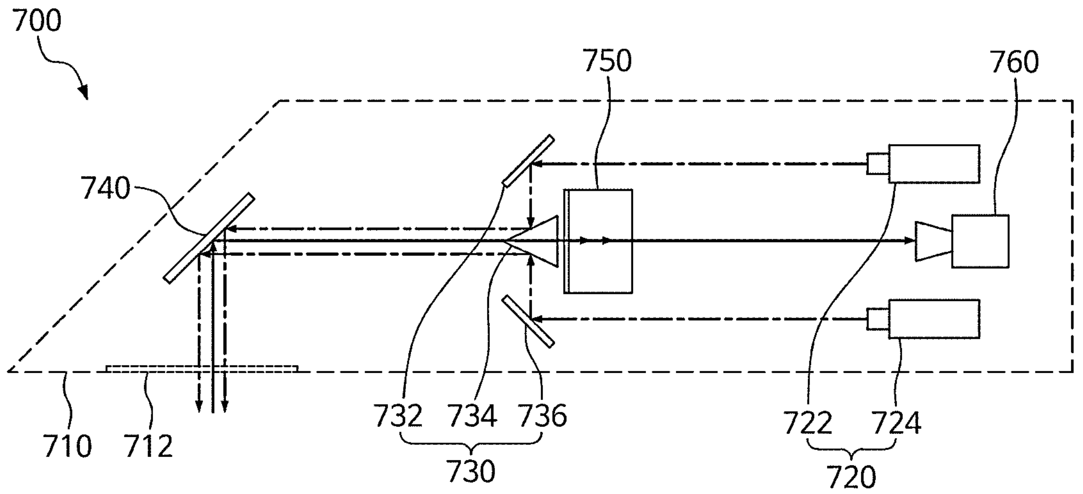
FIG. 7 is a see-through lateral view of an intraoral scanner according to yet another embodiment of the present disclosure.

FIG. 7 is a see-through lateral view of an intraoral scanner 700 according to yet another embodiment of the present disclosure. Configurations of FIG. 7 that overlap with FIG. 2 will be briefly described based on the embodiment illustrated in FIG. 7. As illustrated in FIG. 7, a light source part 720 may be configured to emit light toward an opening part 712 or a first optical system 730. The light source part 720 may include a first light source part 722 and a second light source part 724. Any one ray of light among rays of light emitted from the first light source part 722 and the second light source part 724 may correspond to patterned light or structured light, and other rays of light may correspond to normal light without a pattern. The first light source part 722 and the second light source part 724 may be configured to alternately emit light at predetermined time intervals. Also, the first light source part 722 and the second light source part 724 may be disposed together with an image sensor part 760 at the other end of a case 710 that faces one end of the case at which the opening part 712 is installed and may be disposed to be respectively fixed to an upper portion and a lower portion of the other end inside the case 710 while being symmetrical to each other about the image sensor part 760.

In one embodiment, the first optical system 730 may be configured to reflect light emitted from the light source part 720 toward the opening part 712 through a first reflector 732, a second reflector 734, and a third reflector 736. That is, the first reflector 732 and the third reflector 736 may be configured to reflect light emitted from the light source part 720 toward the second reflector 734. The first reflector 732 may be disposed to be fixed to an upper portion inside the case, and the third reflector 736 may be disposed to be fixed to a lower portion inside the case. Also, the second reflector 734 may include two reflective surfaces each configured to reflect one of the light reflected by the first reflector 732 and the light reflected by the third reflector 736 toward the opening part 712 or a second optical system 740. In this case, a dihedral angle between the reflective surfaces of the second reflector 734 may be configured to form a major angle. The second reflector 734 may be disposed to be spaced apart from the first reflector 732 and the third reflector 736 and fixed to a central portion inside the case 710. That is, light emitted from the light source part 720 may be reflected toward the opening part 712 or the second optical system 740 via the first reflector 732, the third reflector 736, and the second reflector 734 of the first optical system 730.

Light reflected from the second reflector 734 may be reflected toward a subject by the second optical system 740. In this case, light may pass through an opening formed at one side of the opening part 712. Light reflected from the subject positioned outside the case may be reflected again toward a third optical system 750 by the second optical system 740. Light refracted by the third optical system 750 may be reflected toward the image sensor part 760. Here, the third optical system 750 may include the same configuration as the third optical system 250 illustrated in FIG. 2.

As illustrated, the light source part 720 and the second optical system 740 may be disposed to be fixed to both ends of the space inside the case 710. Also, the first optical system 730 disposed at any position between the light source part 720 and the second optical system 740 may be disposed in an area that does not interfere with a path along which light that is reflected from the subject and reflected toward the third optical system 750 by the second optical system 740 passes, that is, a blind area. That is, the first optical system 730 may be disposed in an area that does not overlap with a portion of light reflected from the subject that is incident on the third optical system 750. For example, a first reflector and a second reflector (for example, 252 and 254 in FIG. 2) of the third optical system 750 may be disposed to be spaced apart from each other on a rear surface of the second reflector 234, and a distance between the first reflector and the second reflector (for example, 252 and 254 in FIG. 2) may correspond to a length of the width of the second reflector 234. In this way, by each of the first optical system 730 and the third optical system 750 being appropriately disposed in a blind area instead of a valid optical path while an optical path of the first optical system 730 and an optical path of the third optical system 750 do not interfere with each other, the components inside the case may be more densely arranged.

The exemplary embodiments of the present invention which have been described above are only disclosed for illustrative purposes. Those of ordinary skill in the art to which the present invention pertains may make various modifications, changes, and additions within the spirit and scope of the present invention, and such modifications, changes, and additions also belong to the scope of the claims.

Since various substitutions, alterations, and changes may be made within the scope not departing from the technical spirit of the present invention by those of ordinary skill in the art to which the present invention pertains, the present invention is not limited by the embodiments described above or the accompanying drawings.

What is claimed is:

1. An intraoral scanner comprising:

a case having an opening part formed at a front portion of the intraoral scanner;

a light source part disposed apart from a front portion of the intraoral scanner and configured to emit light;

a first optical system including a first reflector configured to reflect the light emitted from the light source part and a second reflector configured to reflect the light reflected by the first reflector toward the opening part;

a second optical system including one reflector that forms a first optical path with the second reflector, the second optical system being configured to reflect the light reflected from the first optical system toward a subject through the opening part and to reflect the light reflected from the subject toward the inside of the case;

a third optical system configured to reflect the light reflected from the one reflector of the second optical system, the third optical system being disposed such that it forms a pair of second optical paths with the one reflector of the second optical system without interfering with the second reflector forming the first optical path; and an image sensor part configured to detect the light refracted by the third optical system.

2. The intraoral scanner of claim 1, wherein:

the third optical system includes a first reflector and a second reflector configured to reflect the light reflected from the second optical system and a prism configured to refract the light reflected by the first reflector and the second reflector toward the image sensor part; and the first reflector and the second reflector are disposed to be symmetrical to each other about the prism.

3. The intraoral scanner of claim 2, wherein a dihedral angle between the first reflector and the second reflector is configured to form a minor angle.

4. The intraoral scanner of claim 2, wherein positions and directions of the first reflector, the second reflector, and the prism are set so that a plurality of images of the subject each refracted by the prism and detected by the image sensor part do not overlap with each other, and each of the images is entirely visible.

5. The intraoral scanner of claim 1, wherein the first optical system is configured as a rhomboid prism including the first reflector and the second reflector.

6. The intraoral scanner of claim 1, wherein the light source part includes:

a first light source part disposed at an upper portion from the image sensor part; and a second light source part disposed at a lower portion from the image sensor part.

7. The intraoral scanner of claim 6, wherein, in the first optical system:

the first reflector is configured to reflect light emitted from the first light source part;

a third reflector disposed at a position symmetrical to the first reflector about the second reflector and configured to reflect light emitted from the second light source part is further included;

the second reflector includes two reflective surfaces each configured to reflect one of the light reflected by the first reflector and the light reflected by the third reflector toward the opening part; and a dihedral angle between the reflective surfaces of the second reflector is configured to form a major angle.

8. The intraoral scanner of claim 1, wherein the light source part is configured to emit patterned light or structured light.

9. The intraoral scanner of claim 1, wherein the image sensor part is configured to obtain a plurality of stereo images from an image of light reflected from the third optical system.

10. The intraoral scanner of claim 1, wherein virtual central lines of the light source part, the first optical system, the second optical system, the third optical system, and the image sensor part that are projected on a plane of the case are arranged to be aligned on a virtual central line projected on the plane of the case.

11. The intraoral scanner of claim 1, wherein the third optical system is configured to be disposed adjacent to a rear surface opposite to a reflective surface of the second reflector.

* * * * *